United States Patent
Kang et al.

(10) Patent No.: US 8,524,686 B2
(45) Date of Patent: Sep. 3, 2013

(54) COMPOSITION FOR PREVENTION OR TREATMENT OF EYE DISEASES

(75) Inventors: Seung Woo Kang, Seoul (KR); Cheorl-Ho Kim, Daegu (KR); Seok-Jo Kim, Busan (KR)

(73) Assignee: Benebiosis Co., Ltd., Seoul (KR)

( * ) Notice: Subject to any disclaimer, the term of this patent is extended or adjusted under 35 U.S.C. 154(b) by 167 days.

(21) Appl. No.: 13/124,965

(22) PCT Filed: Oct. 16, 2009

(86) PCT No.: PCT/KR2009/005983
§ 371 (c)(1),
(2), (4) Date: Jun. 9, 2011

(87) PCT Pub. No.: WO2010/047500
PCT Pub. Date: Apr. 29, 2010

(65) Prior Publication Data
US 2011/0237543 A1    Sep. 29, 2011

(30) Foreign Application Priority Data

Oct. 20, 2008  (KR) .................. 10-2008-0102660

(51) Int. Cl.
*A61K 31/70*    (2006.01)
(52) U.S. Cl.
USPC .......................................................... 514/54
(58) Field of Classification Search
USPC .......................................................... 514/54
See application file for complete search history.

(56) References Cited

U.S. PATENT DOCUMENTS
5,260,280 A * 11/1993 Isoda et al. .................. 514/25

* cited by examiner

*Primary Examiner* — Elli Peselev
(74) *Attorney, Agent, or Firm* — Clark & Elbing LLP (57) ABSTRACT

Provided is a composition for prophylaxis or treatment of an eye disease comprising a compound represented by General Formula I:

$$S\text{-}(MS)_p\text{-}(MS)_q \qquad \text{General Formula I}$$

wherein S represents sialic acid, and $(MS)_p$ and $(MS)_q$ independently represent a monosaccharide residue.

The compound used as the active ingredient inhibits expression of MMP-9 and inflammation-mediated cytokines (IL-1β, TNF-α, etc.) in corneal epithelial cells and inhibits VEGF-mediated VEGFR-2 activation in human retinal endothelial cells (HREC), thereby exhibiting prophylactic or therapeutic activity for eye diseases such as dry eye syndrome, inflammatory eye disease, neovascularization-associated eye disease and side effects of wearing of contact lenses. Also, because it has no cytotoxicity or skin side effect, the provided composition may be safely used as a pharmaceutical composition, a neutraceutical composition or a food composition. In addition, the composition may be used as a cleaner or a lubricant for contact lenses since it has nonbacterial antiinflammatory activity and ocular contact lubricating activity.

11 Claims, 4 Drawing Sheets

COMPOSITION FOR PREVENTION OR TREATMENT OF EYE DISEASES

CROSS-REFERENCE TO RELATED APPLICATIONS

This application is the U.S. national stage filing under 35 U.S.C. §371 of international application PCT/KR2009/005983, filed Oct. 16, 2009, which claims benefit of Korean Patent Application 10-2008-0102660, filed Oct. 20, 2008.

TECHNICAL FIELD

The present invention relates to a composition for prophylaxis or treatment of eye diseases and an artificial tear composition.

BACKGROUND ART

Dry eye syndrome is a common disease with a prevalence rate of 5.5-15% depending on population, age and diagnosis standard (1,2). This disease is characterized by pain, irregular corneal surface, blurred and fluctuating vision, and increased risk of corneal ulcer (3,4). The change in corneal permeability caused by chronic dry eyes and keratitis sicca resulting from unstable tear film has been known to cause inflammations, which has been demonstrated by increased inflammation-mediated chemokine and cytokine in tears, increased immune activity and expression of adhesion molecules (HLA-DR and inter-cellular adhesion molecule 1 [ICAM-1]) by conjunctival epithelial cells, and increased T lymphocytes in the conjunctiva (5,6). Corneal ulcer resulting from keratoconjunctivitis sicca (KCS) may lead to poor vision, vision loss and, even blindness (7,8). The level and activity of matrix metalloproteinase-9 (MMP-9) are reported to increase greatly not only in the tears of patients with dry eye syndrome (9), but also in the corneal epithelium and tears of experimental dry eye (EDE) mice (10).

Recently, it has been consistently reported that inflammation and apoptosis on ocular surface play an important role in the development of dry eye syndrome (11). Hyperosmotic stress and increased inflammatory cytokines (i.e., interleukin (IL)-1, tumor necrosis factor (TNF)-α and transforming growth factor (TGF)-β) associated with dry eye syndrome have been known to increase the expression of MMP-9 by corneal epithelial cells (12). These chronic inflammatory environments are in part due to the characteristic pathological degeneration of the conjunctival epithelium such as squamous metaplasia and loss of goblet cells (13).

Angiogenesis, a process involving the growth of new blood vessels from pre-existing vessels, is known as a fundamental process in various physiological and pathological conditions including wound healing, embryonic development, chronic inflammation, and tumor development and transition (14,15). Also, angiogenesis is known to be involved in various conditions that may cause loss of vision, such as diabetic retinopathy, macular degeneration, retinopathy of prematurity and retinal vein occlusion (16). New blood vessels are known to grow from pre-existing veins through a series of processes including degradation of the basement membrane (BM) and extracellular matrix (ECM) of endothelial cells by proteases (17,18), proliferation and migration of endothelial cells (19), and formation and occlusion of vascular tubes (20). With regard to vision loss caused by angiogenesis-associated retinal damage, it is known that the suppression of one or more of the above processes is of potential therapeutic value (16).

Figure 1:
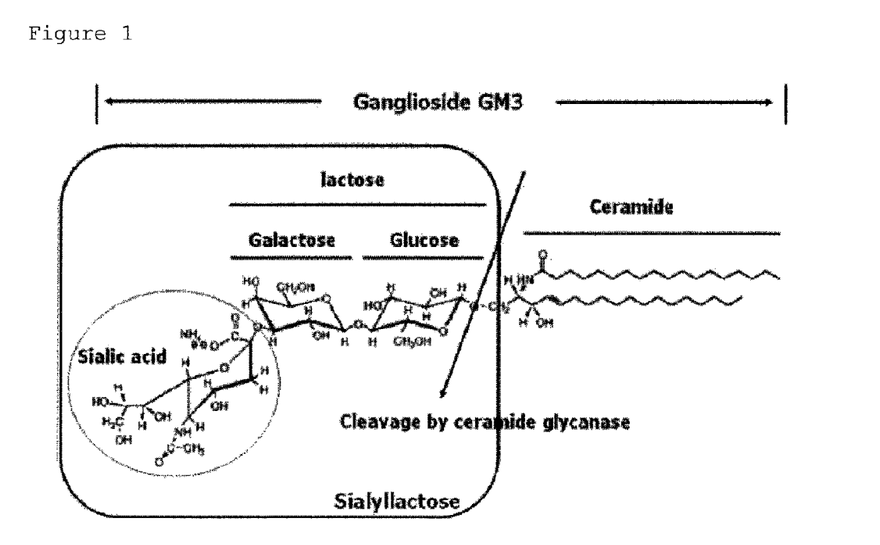
FIG. 1 shows the structure of sialyllactose, an active ingredient of the present invention.

Sialyllactose (Neu5Ac α-2,3-D-Gal β-1,4-D-Glc) (FIG. 1) is a sialic acid including the glycosphingolipid of GM3 ganglioside, and is commonly found in blood plasma and cell membrane of mammals (12,22). However, there has been no research about the action of sialyllactose on dry eye syndrome or other eye diseases.

Throughout this specification, a number of literatures and patent documents are referenced and cited. The disclosure of the cited literatures and patent documents are incorporated herein by reference to more clearly explain the background art and the present invention.

DISCLOSURE

The inventors of the present invention aimed to develop a substance capable of preventing or treating various eye diseases. As a result, the inventors have found that sialyloligosaccharide inhibits expression of MMP-9 and inflammation-mediated cytokines (IL-1β, TNF-α, etc.) in dry eye animal model and inhibits VEGF-mediated VEGFR-2 activation in human retinal endothelial cells, and thus is able to effectively prevent or treat eye diseases such as dry eye syndrome, inflammatory eye disease and neovascularization-associated eye disease and side effects associated with the use of contact lenses.

Accordingly, an object of the present invention is to provide a composition for prophylaxis or treatment of an eye disease.

Another object of the present invention is to provide an artificial tear composition.

Another object of the present invention is to provide a composition for cleaning, lubricating or packaging contact lenses.

Another object of the present invention is to provide a method for prophylaxis or treatment of eye disease.

Another object of the present invention is to provide a method for lubricating or hydrating eyes.

Another object of the present invention is to provide a method for cleaning, lubricating or packaging contact lenses.

DESCRIPTION OF DRAWINGS

The above and other objects, features and advantages of the present invention will become apparent from the following description of preferred embodiments given in conjunction with the accompanying drawings, in which.

BEST MODE

Hereinafter, the embodiments of the present invention will be described in detail with reference to accompanying drawings.

Unless otherwise defined, all terms (including technical and scientific terms) have the meaning as commonly understood by one of ordinary skill in the art. In the following description and drawings, details of well-known features and techniques may be omitted to avoid unnecessarily obscuring the present invention.

In one embodiment, the present invention provides a composition for prophylaxis or treatment of an eye disease comprising a compound represented by General Formula I, a salt thereof, a hydrate thereof or a solvate thereof as an active ingredient:

General Formula I wherein S represents sialic acid, and $(MS)_p$ and $(MS)_q$ independently represent a monosaccharide residue.

In another embodiment of the present invention, the present invention provides method for prophylaxis or treatment of eye an disease comprising administering a composition comprising a compound represented by General Formula I, a salt thereof, a hydrate thereof or a solvate thereof as an active ingredient to a subject:

General Formula I wherein S represents sialic acid, and $(MS)_p$ and $(MS)_q$ independently represent a monosaccharide residue.

The inventors of the present invention aimed to develop a substance capable of preventing or treating various eye diseases. As a result, the inventors have found that sialyloligosaccharide inhibits expression of MMP-9 and inflammation-mediated cytokines (IL-1β, TNF-α, etc.) in dry eye animal model and inhibits VEGF-mediated VEGFR-2 activation in human retinal endothelial cells (HREC), and thus can be used to effectively prevent or treat eye diseases such as dry eye syndrome, inflammatory eye disease and neovascularization-associated eye disease and side effects associated with the use of contact lenses.

In the present invention, the active ingredient is a compound represented by General Formula I. In General Formula I, S represents sialic acid. Sialic acid may be bound to $(MS)_p$ in various manners. Most preferably, it is bound to the monosaccharide compound $(MS)_p$ via α-2,3 linkage. In addition to sialic acid, S may be modified sialic acid. For example, S may be sialic acid with the —OH group at the C4-position modified (e.g. by $C_1$-$C_4$ alkyl). Most preferably, S is unmodified sialic acid.

The monosaccharide compounds $(MS)_p$ and $(MS)_q$ may be any monosaccharide compound known in the art. For example, tetroses (e.g., erythrose and threose), pentoses (e.g., ribose, arabinose, xylose and lyxose) and hexoses (allose, altrose, glucose, mannose, gulose, idose, galactose and talose) are included. The monosaccharide compounds $(MS)_p$ and $(MS)_q$ may be preferably a pentose or a hexose, more preferably a hexose, further more preferably, glucose, mannose or galactose, and most preferably, glucose or galactose. The monosaccharide compounds $(MS)_p$ and $(MS)_q$ may be a D- or L-stereoisomer, most preferably a D-stereoisomer.

$(MS)_p$ and $(MS)_q$ may be the same or different monosaccharide compound. Preferably, they are different monosaccharide compounds.

According to a preferred embodiment of the present invention, $(MS)_p$ is galactose or glucose, and $(MS)_q$ is glucose or galactose. Most preferably, $(MS)_p$ is galactose and $(MS)_q$ is glucose. When $(MS)_p$ is galactose and $(MS)_q$ is glucose, the disaccharide compound lactose is obtained.

The monosaccharide compounds $(MS)_p$ and $(MS)_q$ may be modified or unmodified. For example, a monosaccharide compound with the —OH group bound to acetyl or N-acetyl may be used. Preferably, the monosaccharide compounds $(MS)_p$ and $(MS)_q$ are unmodified monosaccharide compounds.

The most preferred embodiment of the compound represented by General Formula I, which is used as the effective ingredient in the present invention, is sialic acid-galactose-glucose. Sialic acid-galactose-glucose is called sialyllactose.

In the composition of the present invention, in addition to the above-described compound itself, a pharmaceutically acceptable salt, hydrate or solvate thereof may be used as the effective ingredient.

The term "pharmaceutically acceptable salt" refers to a salt of the compound that produces the desired pharmacological effect, i.e. inhibiting expression of MMP-9 and inflammation-mediated cytokines (IL-1β, TNF-α, etc.) in corneal epithelial cells and inhibiting VEGF-mediated VEGFR-2 activation in retinal endothelial cells. The salt is formed by using an inorganic acid (e.g., hydrochloride, hydrobromide and hydroiodide) or an organic acid (e.g., acetate, adipate, alginate, aspartate, benzoate, benzenesulfoate, p-toluenesulfoate, bisulfate, sulfamate, sulfate, naphtalate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, 2-hydroxyethanesulfonate, lactate, maleate, methanesulfonate, 2-naphthalenesulfonate, nicotinate, oxalate, tosylate and undecanoate).

The term "pharmaceutically acceptable hydrate" refers to a hydrate of the compound that produces the desired pharmacological effect. The term "pharmaceutically acceptable solvate" refers to a solvate of the compound that produces the desired pharmacological effect. The hydrate and the solvate may also be prepared using the aforementioned acids.

The composition of the present invention comprising the compound represented by General Formula I or the pharmaceutically acceptable salt, hydrate or solvate thereof as an active ingredient inhibits expression of MMP-9 and inflammation-mediated cytokines (IL-1β, TNF-α, etc.) in corneal epithelial cells and inhibits VEGF-mediated VEGFR-2 activation in HREC, thereby exhibiting prophylactic or therapeutic activity for eye diseases such as dry eye syndrome, inflammatory eye disease and neovascularization-associated eye disease.

According to a preferred embodiment of the present invention, the eye diseases that may be prevented or treated by the composition of the present invention are dry eye syndrome, inflammatory eye disease, retinal neovascularization-associated eye disease and side effects associated with the use of contact lenses.

According to a more preferred embodiment of the present invention, the eye disease that may be prevented or treated by the composition of the present invention is dry eye syndrome.

According to another more preferred embodiment of the present invention, the inflammatory eye disease that may be prevented or treated by the composition of the present invention is meibomian gland dysfunction, Stevens-Johnson syndrome, Sjogren's syndrome, uveitis or keratitis.

According to a more preferred embodiment of the present invention, the retinal neovascularization-associated eye disease that may be prevented or treated by the composition of the present invention is diabetic retinopathy, macular degeneration, retinopathy of prematurity, corneal graft rejection, retrolental fibroplasia, neovascular glaucoma, iris neovascularization, retinal neovascularization, hypoxia, ocular tumor or trachoma. Most preferably, the composition of the present invention inhibits VEGF-mediated VEGFR-2 activation in HREC, and, thereby inhibits retinal neovascularization.

According to another more preferred embodiment of the present invention, the side effects associated with the use of contact lenses that may be prevented or treated by the composition of the present invention are discomfort, dryness, burning feeling, pricking feeling and non-bacterial inflammation caused by the use of contact lenses.

The composition of the present invention may be prepared into a pharmaceutical composition, a neutraceutical composition or a food composition.

According to a preferred embodiment of the present invention, the composition of the present invention is a pharmaceutical composition comprising (a) a pharmaceutically effective amount of the compound represented by General Formula I, the salt thereof, the hydrate thereof or the solvate thereof; and (b) a pharmaceutically acceptable carrier.

As used herein, the term "pharmaceutically effective amount" refers to an amount sufficient to attain the effect or activity of the compound represented by General Formula I, the salt thereof, the hydrate thereof or the solvate thereof.

When the composition of the present invention is prepared into a pharmaceutical composition, the pharmaceutical composition of the present invention comprises a pharmaceutically acceptable carrier. The pharmaceutically acceptable carrier comprised in the pharmaceutical composition of the present invention is one commonly used in formulations and includes, but is not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc. The pharmaceutical composition of the present invention may further comprise, in addition to aforesaid ingredients, a lubricant, a wetting agent, a sweetener, a flavor, an emulsifier, a suspending agent, a preservative, or the like. Suitable pharmaceutically acceptable carriers and formulations are described in detail in Remington's Pharmaceutical Sciences (19th ed., 1995).

The pharmaceutical composition of the present invention may be administered orally or parenterally. In case of parenteral administration, it may be administered through intravenous injection, subcutaneous injection, intramuscular injection, intraperitoneal injection, transdermal administration, mucosal administration, ocular administration, or the like.

An adequate amount of the pharmaceutical composition of the present invention to be administer may vary depending on various factors including formulation method, administration method, age, weight, sex or disease condition of the patient, diet, administration time, administration route, elimination rate and response sensitivity. The active ingredient of the present invention may be preferably administered, for an adult, in an amount of 0.001-100 mg/kg (body weight) per day, more preferably 0.01-80 mg/kg (body weight), most preferably 0.1-60 mg/kg (body weight). Also, under the discretion of the physician or pharmacist, it may be administered once or several times per day. Especially, in case of ocular administration, about 0.001-3% (w/v, this is also the same hereinbelow), preferably about 0.01-1%, of the composition is administered once or several times per day.

The pharmaceutical or neutraceutical composition of the present invention may be prepared according to a method that may be conventionally carried out by those skilled in the art in single-dose forms or in multi-dose packages using a pharmaceutically acceptable carrier and/or excipient.

According to a preferred embodiment of the present invention, a formulation of the composition of the present invention may be in the form of a solution, suspension, syrup, emulsion, liposome, extract, dust, powder, granule, tablet, sustained-release formulation, eye drop, capsule, contact lens cleaner or contact lens lubricant, and may further comprise a dispersant or a stabilizer.

More specifically according to administration route, a solid formulation for oral administration may be in the form of a capsule, tablet, pill, dust and granule. In the solid formulation, the active compound may be mixed with one or more inert pharmaceutically acceptable excipient(s) or carrier(s) (e.g., sodium citrate or dicalcium phosphate) and/or a) filler or extender (e.g., starch, lactose, sucrose, glucose, mannitol and silicic acid), b) binder (e.g., carboxymethylcellulose, alginate, gelatin, polyvinylpyrrolidone, sucrose and gum arabic), c) humectant (e.g., glycerol), d) disintegrant (e.g., agar-agar, calcium carbonate, potato or tapioca starch, alginic acid, certain silicate and sodium carbonate), e) solution retarder (e.g., paraffin), f) absorption accelerator (e.g., quaternary ammonium compound), g) wetting agent (e.g., cetyl alcohol and glycerol monostearate), h) adsorbent (e.g., kaolin and bentonite) and i) lubricant (e.g., talc, calcium stearate, magnesium stearate, solid polyethylene glycol, sodium lauryl sulfate and mixture thereof). In the case of capsules, tablets and pills, the formulation may further comprise a buffer agent.

Further, in addition to an excipient such as lactose or milk sugar, polyethylene glycol or other polymer may be used in a soft or hard gelatin capsule as a filler.

Solid administration forms such as tablet, sugar-coated tablet, capsule, pill and granule may be coated with enteric coating or other coat well known in the pharmaceutical field. The coating may optionally comprise an opacifier, and the composition may be formulated such that only the active ingredient is released at a particular site in the gastrointestinal tract in a sustained manner or preferentially. Also, if necessary, the active compound may be prepared into microcapsule together with the one or more excipient(s).

Especially, in the case of ocular administration, the composition of the present invention may be mixed with purified water, isotonic agent (e.g., sodium chloride, glycerin, etc.), surfactant (e.g., Polysorbate 80, polyoxyethylene alkyl ether, etc.), preservative (e.g., sodium edetate, sodium sorbate, etc.), buffer agent (e.g., sodium phosphate, etc.), pH regulator (e.g., hydrochloric acid, sodium hydroxide, etc.) and other customary pharmaceutical components to be prepared into an eye drop by ordinary method. The liquid property is preferred to be near neutral pH (pH 5 to 8), and the osmotic pressure is also preferred to be near 1.

Liquid formulations for oral administration include pharmaceutically acceptable emulsion, solution, suspension, syrup and elixir. In addition to the active compound, the liquid formulation may comprise an inert diluent commonly used in the art such as, but not limited to, water or other solvent, solubilizing agent and emulsifier (e.g., ethyl alcohol, isopropyl alcohol, ethyl carbonate, ethyl acetate, benzyl alcohol, benzyl benzoate, propylene glycol, 1,3-butylene glycol, dimethylformamide, oil (in particular, cottonseed, groundnut, corn, germ, olive, castor or sesame oil), glycerol, tetrahydrofuryl alcohol, polyethylene glycol and fatty acid ester of sorbitan, and mixtures thereof. Besides the inert diluent, the oral composition may also comprise an adjuvant such as a wetting agent, an emulsifier, a suspending agent, a sweetener, a flavor and a perfume.

A formulation for rectal or vaginal administration is preferably a suppository which can be prepared by mixing the compound of the present invention with suitable non-irritating adjuvant or carrier (e.g., cocoa butter, polyethylene glycol or suppository wax) which is solid at ambient temperature but liquify at body temperature and therefore melts in the rectum or vaginal cavity and releases the active compound.

Formulations suitable for parenteral injection may include a physiologically acceptable sterile aqueous or oleaginous solution, dispersion, suspension or emulsion, and sterile powder which can be dissolved or dispersed in to prepare sterile injectable solution or dispersion. Examples of suitable aqueous or oleaginous carrier, diluent, solvent or vehicle include water, ethanol, polyol (propylene glycol, polyethylene glycol, glycerol, etc.), vegetable oil (olive oil), injectable organic ester (e.g., ethyl oleate), and adequate mixtures thereof.

Further, the composition of the present invention may comprise an adjuvant such as a preservative, a wetting agent, an emulsifier and a dispersant. Prevention of the action of microorganisms may be ensured by the inclusion of various antibacterial and antifungal agents (e.g., paraben, chlorobutanol, phenol, sorbic acid, etc.). It may be also desirable to include an isotonic agent such as sugar, sodium chloride, etc. In addition, prolonged absorption of the injectable formulation may be attained by the inclusion of an agent that, delay absorption (e.g., aluminum monostearate and gelatin).

A suspension, in addition to the active compound, may comprise a suspending agent (e.g., ethoxylated isostearyl alcohol, polyoxyethylene sorbitol and sorbitan ester, microcrystalline cellulose, aluminum metahydroxide, bentonite, agar-agar and tragacanth, and mixtures thereof).

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

An injectable depot form is made by forming microencapsulated matrices of the drug in biodegradable polymers such as polylactide-polyglycolide. The rate of drug release may be determined depending on the ratio of the drug to polymer, and the nature of the particular polymer employed.

Examples of other biodegradable polymer include poly(orthoester) and poly(anhydride). A depot injectable formulation is also prepared by entrapping the drug in liposomes or microemulsions that are compatible with body tissue.

An injectable formulation may be sterilized by, for example, filtration through a bacteria-retaining filter, or by incorporating a sterilizing agent in the form of a sterile solid composition that can be dissolved or dispersed in sterile water or some other sterile injectable medium immediately before use.

According to a preferred embodiment of the present invention, the composition of the present invention is a composition for oral administration, and is in the form of a liposome or sustained-release formulation.

According to another preferred embodiment of the present invention, the composition of the present invention is a composition for parenteral administration, and is in the form of a liposome, sustained-release formulation or eye drop.

The pharmaceutical composition of the present invention may be encapsulated in a liposome to provide stability for drug delivery. The liposome employed in the present invention may be prepared from a mixture of polyol, surfactant, phospholipid, fatty acid and water (Prescott, Ed., *Methods in Cell Biology*, (XIV), p. 33et seq. (1976)).

The polyol used to prepare the liposome is not particularly limited, and preferably includes propylene glycol, dipropylene glycol, 1,3-butylene glycol, glycerin, methylpropanediol, isoprene glycol, pentylene glycol, erythritol, xylitol and sorbitol, most preferably propylene glycol.

The surfactant which can be used in the preparation of the liposome may be any surfactant known in the art, and examples thereof include an anionic surfactant, a cationic surfactant, an amphoteric surfactant and a non-ionic surfactant, preferably an anionic surfactant and a non-ionic surfactant. Specific examples of the anionic surfactant include alkyl acyl glutamate, alkyl phosphate, alkyl lactate, dialkyl phosphate and trialkyl phosphate. Specific examples of the non-ionic surfactant include alkoxylated alkyl ether, alkoxylated alkyl ester, alkyl polyglycoside, polyglyceryl ester and sugar ester. Most preferably, polysorbates are used as the non-ionic surfactant.

The phospholipid, another component used in the preparation of the liposome, is an amphoteric lipid, and includes natural phospholipids (e.g., egg lecithin, soybean lecithin or sphingomyelin) and synthetic phospholipids (e.g., dipalmitoylphosphatidylcholine or hydrogenated lecithin), preferably lecithin. More preferably, the lecithin is naturally occurring saturated or unsaturated lecithin extracted from soybean or egg yolk. In general, naturally occurring lecithin contains 23-95% of phosphatidylcholine and not more than 20% of phosphatidylethanolamine.

The fatty acid used in the preparation of the liposome is a higher fatty acid, preferably a saturated or unsaturated fatty acid having a $C_{12}$-$C_{22}$ alkyl chain, and includes, for example, lauric acid, myristic acid, palmitic acid, stearic acid, oleic acid and linoleic acid. The water used in the preparation of the liposome is, in general, deionized distilled water.

The liposome may be prepared by various methods known in the art. Most preferably, it is prepared by applying a mixture including the aforesaid components in a high-pressure homogenizer.

Thus prepared liposome system is advantageous in that it can maximize drug delivery by dissolving various poorly soluble materials and, at the same time, stabilizing unstable materials.

The pharmaceutical composition of the present invention may be prepared into a sustained-release formulation to continuously maintain an effective blood level of the active ingredient, thereby reducing the number of medication and improving compliance.

The sustained-release formulation is prepared by adding, in addition to the active ingredient of the present invention, a sustained-release carrier and other adjuvant. The sustained-release carrier used in the present invention may be various sustained-release carriers known in the art, preferably polyethylene oxide.

The other adjuvant used to prepare the sustained-release formulation may be a diluent carrier commonly used in the pharmaceutical field. Examples of the diluent carrier used for this purpose include lactose, dextrin, starch, microcrystalline cellulose, calcium hydrogen phosphate, calcium carbonate, starch, silicon dioxide, etc. In addition, a glidant for improving flowability, such as zinc stearate or magnesium stearate, or other adjuvant that may be used in the pharmaceutical field may be included.

In case the composition of the present invention is prepared into a food composition (or neutraceutical composition), in addition to the compound represented by General Formula I as the active ingredient, ingredients conventionally used in food preparation, for example, protein, carbohydrate, fat, nutrient, seasoning and flavor, may be included. Examples of the carbohydrate include monosaccharides, e.g., glucose, fructose, etc.; disaccharides, e.g., maltose, sucrose, oligosaccharide, etc.; and polysaccharides, such as sugars, e.g., dextrin, cyclodextrin, etc. and sugar alcohols, e.g., xylitol, sorbitol, erythritol, etc. The flavor may be a natural flavor [thaumatin or stevia extract (e.g., rebaudioside A, glycyrrhizin, etc.]) or a synthetic flavor (saccharin, aspartame, etc.).

In case the food composition of the present invention is prepared into a drink, in addition to the compound of the present invention represented by General Formula I, for example, citric acid, liquid fructose, sucrose, glucose, acetic acid, malic acid, fruit juice, eucommia extract, jujube extract, licorice extract, etc. may be further included.

According to another embodiment of the present invention, the present invention provides an artificial tear composition comprising a compound represented by General Formula I, a salt thereof, a hydrate thereof or a solvate thereof as an effective ingredient:

$$S\text{-}(MS)_p\text{-}(MS)_q \qquad \text{General Formula I}$$

wherein S represents sialic acid, and $(MS)_p$ and $(MS)_q$ independently represent a monosaccharide residue.

According to another embodiment of the present invention, the present invention provides a method for lubricating or hydrating eyes comprising topically applying an artificial tear composition comprising a compound represented by General Formula I, a salt thereof, a hydrate thereof or a solvate thereof as an effective ingredient to eyes:

$$S\text{-}(MS)_p\text{-}(MS)_q \qquad \text{General Formula I}$$

wherein S represents sialic acid, and $(MS)_p$ and $(MS)_q$ independently represent a monosaccharide residue.

In the artificial tear composition of the present invention, the compound represented by General Formula I, the salt thereof, the hydrate thereof or the solvate thereof, which is employed as the effective ingredient, is the same as the effective ingredient of the composition of the present invention for prophylaxis or treatment of eye disease. Therefore, a description thereabout will be omitted to avoid unnecessary redundancy.

According to a preferred embodiment of the present invention, the effective ingredient included in the artificial tear composition of the present invention promotes secretion of tears from the lachrymal gland, thereby exhibiting prophylactic or therapeutic activity for dry eye syndrome.

The artificial tear composition of the present invention may further comprise an electrolyte, a non-ionic surfactant, an antibacterial agent, a borate/polyol complex or a low molecular weight amino acid.

The electrolyte included in the artificial tear composition simulates the salt content of natural tear fluid, and includes ions contained in the natural tear fluid. For example, the electrolyte employed in the present invention may be potassium, calcium, magnesium and zinc, and their concentrations are described in U.S. Pat. No. 5,403,598.

The non-ionic surfactant included in the composition of the present invention lowers surface tension of the composition of the present invention and enhances the spreading of the composition over the surface of the cornea. The non-ionic surfactant may be any surfactant known in the art, preferably one having an HLB value of 15 or greater. Examples of suitable non-ionic surfactants include polysorbates such as Polysorbate 80 (Tween 80) and block copolymers derived from the addition of ethylene oxide and propylene oxide to ethylenediamine. The artificial tear composition of the present invention will contain the non-ionic surfactant in an amount sufficient to provide the composition with a surface tension of from about 38 to about 45 dynes/cm, which corresponds to the surface tension of the natural tear fluid.

The artificial tear composition of the present invention may be prepared into a single-dose product or a multi-dose product. The single-dose product does not need an antibacterial preservative to maintain the sterility of the composition, but the multi-dose product may need the antibacterial preservative.

A preferred antibacterial preservative employed in the composition of the present invention is polyquaternium-1, in an amount of 0.1 to 10 ppm. The composition of the present invention further comprises a borate/polyol complex or a low molecular weight amino acid to enhance the antibacterial activity of the antibacterial preservative.

The borate/polyol complex is included in an amount of 0.5 to 6.0 wt %, preferably 1.0 to 2.5 wt %, based on the total weight of the composition. The molar ratio of borate to polyol is 1:0.1 to 1:10, preferably 1:0.25 to 1:2.5. As used herein, the borate refers to boric acid, salts of boric acid and other pharmaceutically acceptable borates, or combinations thereof, preferably boric acid, sodium borate, potassium borate, calcium borate, magnesium borate and combinations thereof. The polyol includes various polyols known in the art, preferably sugars, sugar alcohols and sugar acids, more preferably mannitol, sorbitol, propylene glycol and glycerol, and most preferably glycerol.

The low molecular weight amino acid used in the composition of the present invention to enhance the antibacterial activity may be included in an amount of 0.01 to 2.5 w/v %, more preferably 0.1 to 1.0 w/v %. The molecular weight of the low molecular weight amino acid is preferably from 75 to 250. More preferably, the low molecular weight amino acid is glycine.

The artificial tear composition of the present invention is prepared to have a pH and osmolality compatible to the eye. Preferably, the pH is from 6.8 to 7.8, and the osmolality is from 250 to 350 mOsm/kg.

The artificial tear composition of the present invention is prepared to have an enhanced viscosity, so as to increase the retention time of the composition and increase the comfort experienced by the patient when the composition is applied to the eye. Preferably, the viscosity is from 1 to 20 cps, more preferably from 2 to 20 cps, and most preferably from 5 to 20 cps.

The artificial tear composition of the present invention may be applied topically to the cornea to prevent or treat dry eye syndrome. It may also be utilized as an ocular moisture drop or an ocular lubricant. The composition is applied by placing one or two drops on the cornea.

According to another embodiment of the present invention, the present invention provides a composition for cleaning, lubricating or packaging contact lenses comprising a compound represented by General Formula I, a salt thereof, a hydrate thereof or a solvate thereof:

$$S\text{-}(MS)_p\text{-}(MS)_q \qquad \text{General Formula I}$$

wherein S represents sialic acid, and $(MS)_p$ and $(MS)_q$ independently represent a monosaccharide residue.

According to another embodiment of the present invention, the present invention provides a method for cleaning, lubricating or packaging contact lenses comprising contacting a composition comprising a compound represented by General Formula I, a salt thereof, a hydrate thereof or a solvate thereof with contact lenses:

General Formula I wherein S represents sialic acid, and $(MS)_p$ and $(MS)_q$ independently represent a monosaccharide residue.

The composition for cleaning contact lenses of the present invention may comprise a surfactant, as a main component, and a compound represented by General Formula I, a salt thereof, a hydrate thereof or a solvate thereof, as an auxiliary component. Various surfactants having cleaning activity known in the art, including anionic, cationic, non-ionic and amphoteric surfactants, may be included as the main component. Representative anionic surfactant include sulfated surfactants, sulfonated surfactants, and physiologically accepted salts thereof providing superior cleaning activity for lipids, proteins and other deposits on the contact lenses. Examples include sodium lauryl sulfate, sodium laureth sulfate (sulfated and ethoxylated sodium salt of lauryl alcohol), ammonium laureth sulfate (sulfated and ethoxylated ammonium salt of lauryl alcohol), sodium trideceth sulfate (sulfated and ethoxylated sodium salt of tridecyl alcohol), sodium dodecylbenzenesulfonate, disodium lauryl or laureth sulfosuccinate (disodium salt of lauryl or ethoxylated lauryl alcohol half ester of sulfosuccinic acid), disodium oleamido sulfosuccinate, and dioctyl sodium sulfosuccinate (sodium salt of diester of 2-ethylhexyl alcohol and sulfosuccinic acid).

Non-ionic surfactants having good cleaning activity include certain polyoxyethylene, polyoxypropylene block copolymer (poloxamer) surfactants, including various surfactants available under the trade name Pluronic from BASF Corporation (e.g., Pluronic P104 or L64).

The composition of the present invention may include a cationic surfactant. Representative cationic surfactants include triquaternary phosphate esters. Additionally, the composition may include an amphoteric surfactant. Amphoteric surfactants include imidazoline derivatives and N-alkylamino acids.

In the composition for lubricating contact lenses of the present invention, the compound represented by General Formula I, the salt thereof, the hydrate thereof or the solvate thereof promotes secretion of tears from the lachrymal gland, as described above. The secreted tears form a tear film on the surface of the contact lenses and thus provide a lubricating effect. Therefore, the compound represented by General Formula I, the salt thereof, the hydrate thereof or the solvate thereof may be used in the lubricating composition, particularly as an effective ingredient.

The composition for packaging contact lenses of the present invention is an aqueous solution used for packaging contact lenses, and comprises, in general, saline, other buffer solution and deionized water, without being limited thereto. Preferably, the packaging composition of the present invention is a saline containing a salt selected from sodium chloride, sodium borate, sodium phosphate, disodium hydrogen phosphate, sodium dihydrogen phosphate or comparable potassium salts. These components are mixed such that an addition of an acid or base results in relatively less change in pH, thereby forming a buffer solution consisting of an acid and a conjugate base thereof. The buffer solution may further contain 2-(N-morpholino)ethanesulfonic acid (MES), sodium hydroxide, 2,2-bis(hydroxymethyl)-2,2',2"-nitrilotriethanol, N-tris(hydroxymethyl)methyl-2-aminoethanesulfonic acid, citric acid, sodium citrate, sodium carbonate, sodium bicarbonate, acetic acid, sodium acetate, or mixtures thereof.

According to another embodiment of the present invention, the present invention provides contact lenses the surface of which is coated with a compound represented by General Formula I, a salt thereof, a hydrate thereof or a solvate thereof:

General Formula I wherein S represents sialic acid, and $(MS)_p$ and $(MS)_q$ independently represent a monosaccharide residue.

As described above, since the compound represented by General Formula I, the salt thereof, the hydrate thereof or the solvate thereof, which is employed as the effective ingredient in the present invention, has a use for prophylaxis or treatment of eye disease, the compound may be coated on contact lenses to prevent or treat eye diseases.

The contact lenses the surface of which is coated with a compound represented by General Formula I, a salt thereof, a hydrate thereof or a solvate thereof, as the effective ingredient for prophylaxis or treatment of eye disease, include (i) gas-permeable hard or rigid corneal type lenses manufactured from polymerization of an acryl ester such as polymethyl methacrylate (PMMA), silicone acrylate and fluorosilicone methacrylate and (ii) gel type, hydrogel type or soft type lenses manufactured from a polymer having hydrophilic repeating units, prepared from 2-hydroxyethyl methacrylate (HEMA) or other hydrophilic monomer, such that the lenses have a water content of 20 wt % or more.

Mode for Invention

The examples and experiments will now be described. It will be apparent to those skilled in the art that the following examples and experiments are for illustrative purposes only and not intended to limit the scope of the present invention.

Test Materials and Test Methods

Cell Culturing

Human retinal endothelial cells (HREC) were acquired from Sciencell (USA). The cells were cultured in sterilized endothelial cell medium (ECM, Sciencell, USA), and kept in a humidified 5% $CO_2$ incubator at 37° C. Passages 4 to 6 of the HREC were used for testing.

Mouse Model of Dry Eye 6 to 8 weeks old C57BL/6 mice (Central Lab Animal, Seoul, Korea) were used for mouse model for dry eye syndrome. All animals were treated according to the ARVO Statement for the Use of Animals in Ophthalmic and Vision Research. Experimental dry eye (EDE) was induced by subcutaneous injection of 0.5 mg/0.2 mL scopolamine hydrobromide (Sigma-Aldrich, St. Louis, Mo.) in alternating hindquarters administered four times a day (9 AM, 12 AM, 3 PM and 6 PM) and by exposure to air and ≦40% ambient humidity for 18 hours per day, as previously reported (23). Four experimental groups were evaluated: untreated group (UT), EDE group (control), EDE+sialyllactose (1 mg/kg) group and EDE+sialyllactose (5 mg/kg) group.

Measurement of Tear Production

Tear production was measured with cotton thread (Zone-quick; Oasis). The thread was held with jeweler forceps and applied to the ocular surface in the lateral canthus for 60 seconds. Wetting of the thread was measured in millimeters, using the scale on the cotton thread.

RNA Isolation and RT-PCR

Corneal and conjunctival epithelial cells acquired from six eyes per each test group. Total RNA was isolated using Trizol reagent (JBI Co., Korea) and kept at −80° C. until use. cDNA was synthesized by reverse transcriptase with an oligo dT-adaptor primer from an RNA PCR kit (Bioneer, Korea) according to the manufacturer's recommended protocol. First-strand cDNA synthesis was performed using primer pairs specific for murine IL-1β, TNF-α, MMP-9 and GAPDH mRNA (Table 1). In RT-PCR assay, utilization of the same quantity of mRNA was confirmed by analyzing expression level of mGAPDH. PCR product was separated by electrophoresis on 2% agarose gel containing 1×TAE buffer and EtBr.

TABLE 1

Mouse primer sequence used for RT-PCR

| Gene | Gene Bank Accession No. | Sense primer | Antisense primer | PCR product (bp) |
|---|---|---|---|---|
| IL-1β | M15131 | TGAGCTGAAAGCTCTCCACC | CTGATGTACCAGTTGGGGAA | 297 |
| TNF-α | M11731 | TCAGCCTCTTCTCATTCCTG | TGAAGAGAACCTGGGAGTAG | 333 |
| MMP-9 | NM_013599 | CGACGACGACGAGTTGTG | CTGTGGTGCAGGCCGAATAG | 300 |
| GAPDH | M32599 | GCCAAGGTCATCCATGACAAC | GTCCACCACCCTGTTGCTGTA | 498 |

Zymography

In order to determine the relative concentration of gelatinases in corneal and conjunctival epithelial cells, SDS-PAGE gelatin zymography was performed by using a previously reported method (24). Tissue was homogenized in a sample buffer containing 50 mM Tris-HCl (pH 8.0), 150 mM NaCl, 0.02% $NaN_3$, 100 mg/mL phenylmethylsulfonyl fluoride (PMSF) and 1% Triton X-100. Cell lysate was centrifuged at 10,000×g, at 4° C. for 10 minutes, and separated by electrophoresis on 8% polyacrylamide gel containing gelatin (0.5 mg/mL). The gel was immersed in 0.25% Triton X-100 at ambient temperature for 30 minutes to remove SDS, and reacted overnight at 37° C. in a lysis buffer containing 50 mM Tris-HCl, 150 mM NaCl, 10 mM $CaCl_2$, 2 $ZnSO_4$, 0.01% Brij-35 and 5 mM PMSF (serine protease inhibitor) so that protease could break down the substrate. The gel was washed with distilled water, stained with 0.25% Coomassie Brilliant Blue R-250 in 40% isopropanol for 2 hours, and then destained with 10% acetic acid.

Western Blotting Assay

HREC were homogenized in a buffer containing 50 mM Tris-HCl (pH 8.0), 150 mM NaCl, 0.02% $NaN_3$, 100 μg/mL PMSF, 1 μg/mL aprotinin and 1% Triton X-100. Protein concentration was measured using a Bio-Rad protein assay (Bio-Rad, USA). Thirty (30) μg of the total cell lysate sample was separated by SDS-PAGE based on size, and subjected to electrophoretic migration toward a nitrocellulose membrane using a Hoefer electrophoresis system (Amersham Biosciences, UK). For detection of target protein, the membrane was reacted with p-AKT, ERK, p-ERK, VEGFR-2 (flk-1, Q-20), VE-cadherin, FAK, paxillin, vincullin (SantaCruz Biotechnology, USA) and p-VEGFR-2 (Cell Signaling Tech., USA) antibodies. Detection was carried out using secondary horseradish peroxidase-bound anti-rabbit IgG antibody, anti-goat IgG antibody and anti-mouse IgG antibody (SantaCruz Biotechnology, USA), and using ECL chemiluminescence system (Amersham Biosciences, UK).

Immunofluorescence Microscopy

HREC were inoculated onto 12 mm n-sterilized, gelatin-coated coverslip of 6-well tissue culture plate. In the presence or absence of sialyllactose, HREC were immobilized with 3.7% formalin with or without treatment with VEGF. Then, the cells were passed through 0.5× Triton X-100 in PBS and washed three times with PBS. Non-specific sites were blocked with PBS-containing 1% bovine serum albumin, while gently shaking at ambient temperature for 30 minutes. After immersing the cells in a solution of FAK, paxillin, vincullin and VE-cadherin antibodies, the cells were incubated overnight at 4° C. After washing with PBS, the cells were further reacted with Alexa Flour 594-conjugate goat anti-mouse IgG (Molecular Probes, USA) and Alexa Flour 488-conjugate goat anti-rabbit IgG (Molecular Probes, USA) at ambient temperature for 1 hour. After washing with PBS, analysis was carried out by fluorescence microscopy. Primary antibodies previously bound to antigens or secondary antibodies were used as negative control.

Tube Formation Assay

Sialyllactose's inhibition effect against HREC's capillary-like network induced by VEGF was investigated using Matrigel-coated 24-well culture plate. Matrigel (13.9 mg/mL) was melted overnight at 4° C. and mixed with ECM medium at a ratio of 1:1. After adding 70 μL of Matrigel (6.95 mg/mL) diluted with ECM to each well of the 24-well culture plate, polymerization was performed for 1 hour at 37° C. For evaluation of tube formation, HREC were detached from the tissue culture plate, washed, resuspended in ECM medium containing 1% FBS ($1\times10^4$ cells/well), and added to the Matrigel-coated well in the presence or absence of VEGF along with sialyllactose at various concentrations. The plate was incubated in a 5% $CO_2$ incubator for 24 hours at 37° C., and capillary-like tube formed in each well of the plate was photographed using a Nikon optical microscope.

Test Results

Sialyllactose's Effect on Tear Production

Tear production at the ocular surface in the lateral canthus from the UT, EDE and two treatment groups (6 eyes/group/experiment, in four different sets of experiments) was measured with cotton thread. Scopolamine-induced EDE mice showed decreased tear production than the UT group. In contrast, the test groups (EDE+sialyllactose) showed statistically significant increased tear production (Table 2).

TABLE 2

Sialyllactose's effect on tear production

| Group (n = 6) | Tear production (mm)* |
|---|---|
| UT (no dry eye treatment) | 2.11 ± 0.21 |
| EDE | 0.98 ± 0.38 |
| EDE + sialyllactose (1 mg/kg) | 1.55 ± 0.48 |
| EDE + sialyllactose (5 mg/kg) | 1.45 ± 0.34 |

*Thread's wet length

Sialyllactose's Effect on MMP-9 and Inflammation-Mediated Cytokine

Figure 2:
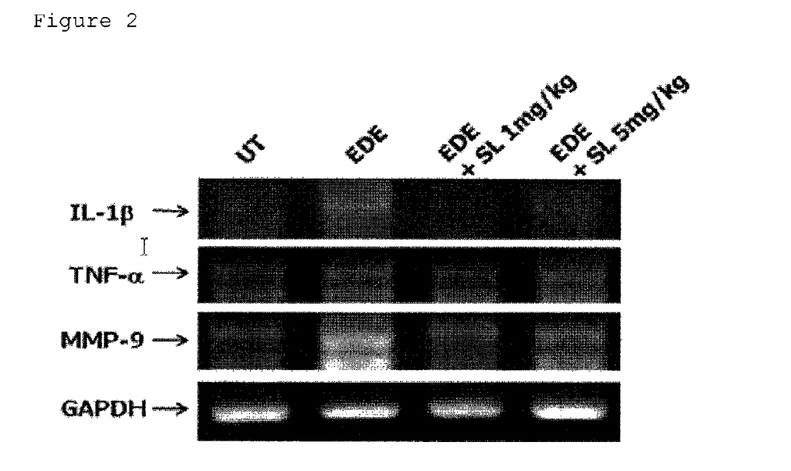
FIG. 2 shows RT-PCR result showing RNA expression for MMP-9, TNF-α and IL-1β in corneal epithelial cells in untreated group (UT) and experimental dry eye group (EDE) [SL stands for sialyllactose]

The level of RNA transcripts encoding MMP-9, IL-1β, TNF-α and the housekeeping gene GAPDH were evaluated by RT-PCR using the total RNA of the corneal epithelial cells obtained from each group (UT, EDE and EDE+sialyllactose). When the EDE group was treated with sialyllactose, the level of MMP-9, IL-1β and TNF-α transcripts decreased (FIG. 2). Of the two treatment groups, the EDE+sialyllactose (5 mg/kg) group showed a larger decrease in the expression of the genes.

Sialyllactose's Effect on Corneal MMP-9 Expression in EDE

Figure 3:
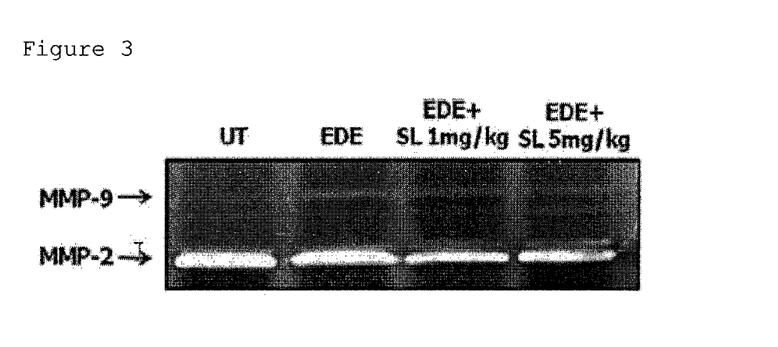
FIG. 3 shows zymogram showing two MMP-9 bands in untreated group (UT) and experimental dry eye group (EDE) [SL stands for sialyllactose]

Gelatinolytic activity (105 kDa gelatinolytic band corresponds to murine MMP-9) was evaluated in corneal and conjunctival epithelial cells acquired from the UT, EDE and two treatment groups. The zymography showed that the cornea of the EDE group mice had higher gelatinolytic activity. In contrast, the EDE+sialyllactose (1 mg/kg) group and the EDE+sialyllactose (5 mg/kg) group showed decreased gelatinolytic activity in corneal and conjunctival epithelial cells, and the UT group showed no decrease of gelatinolytic activity at all (FIG. 3).

Figure 4:
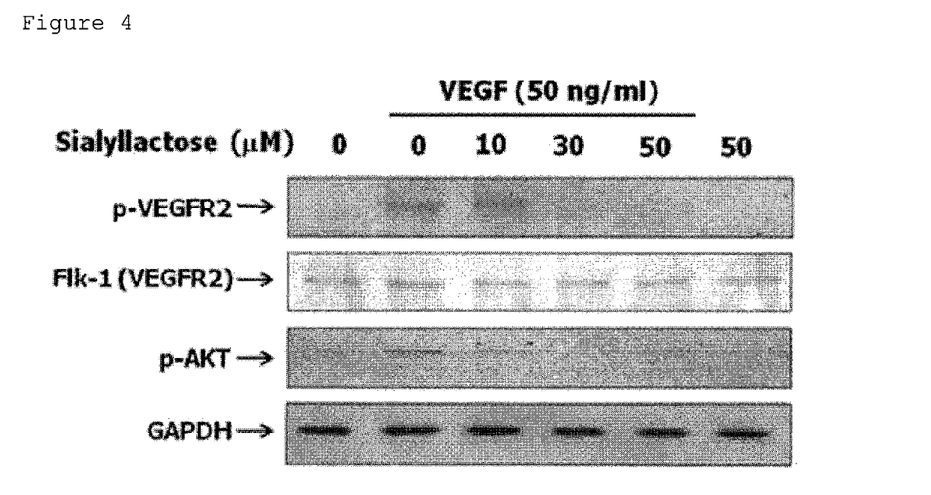
FIG. 4 shows SDS-PAGE result showing sialyllactose's inhibition effect of VEGF-induced VEGFR-2 phosphorylation.

Inhibition of VEGFR-2 and VEGF-mediated Signal Pathway Activation by Sialyllactose in VEGF-Stimulated HREC VEGF-mediated VEGFR-2 activation plays an important role in tumor angiogenesis via the activation of VEGFR-2 downstream signal pathways in endothelial cells (25). The VEGF-mediated VEGFR-2 activation activates PI-3K/AKT-dependent cell migration (26). In addition, the VEGF-induced cell survival of endothelial cells is associated with PI-3K/AKT activation as a VEGFR-2 downstream activation (27). Accordingly, the inventors of the present invention investigated whether the VEGFR-2 activation on the surface of the VEGF-induced endothelial cells was regulated by sialyllactose. As seen in FIG. 4, sialyllactose strongly reduced VEGF-stimulated VEGFR-2 phosphorylation in endothelial cells in a concentration-dependent manner. Further, the inventors of the present invention investigated whether the VEGF-stimulated signal pathway activation was regulated by sialyllactose. As seen in FIG. 4, sialyllactose markedly reduced the VEGF-induced AKT activation, which is associated with the survival, migration and proliferation of the endothelial cells.

These results show that sialyllactose is associated with anti-angiogenic activity by suppressing various downstream signals induced by VEGF-enhanced VEGFR-2 and VEGF-mediated signal pathway activation in HREC.

Sialyllactose's Inhibition Effect Against VEGF-induced Tube Formation in HREC

Figure 5:
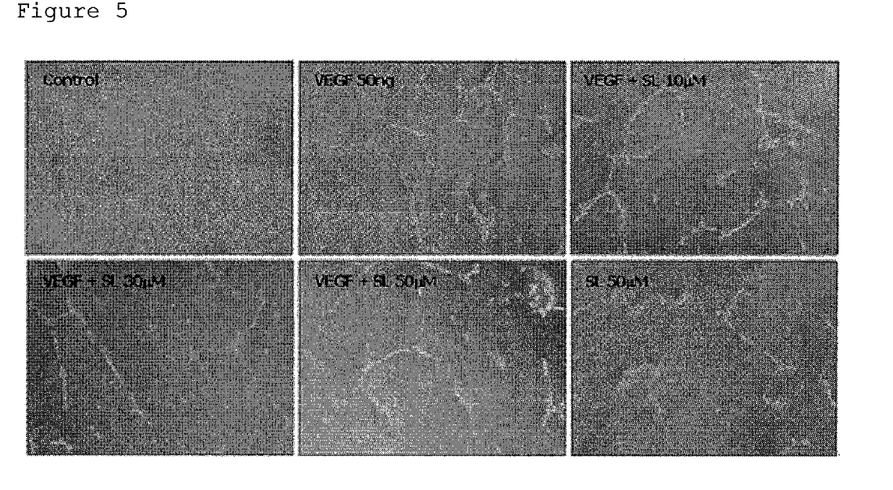
FIG. 5 shows Nikon optical micrographs showing inhibition effect of VEGF-induced tube formation in human retinal endothelial cells (HREC) in vitro.

The VEGF-mediated VEGFR-2 activation is closely associated with the angiogenic action of endothelial cells such as proliferation, migration, survival and tube formation (25). Accordingly, the inventors of the present invention investigated the anti-angiogenic action of sialyllactose in the aspect of VEGF-stimulated proliferation, migration and tube formation of HREC. As seen in FIG. 5, when HREC were placed on growth factor-deficient Matrigel in the presence of VEGF, VEGF formed long and strong tube-like structure, in much more cells as compared to the control group. Sialyllactose significantly reduced the width and length of the tube in VEGF-stimulated HREC in a concentration-dependent manner. This result shows that sialyllactose inhibits VEGF-induced in vitro angiogenesis in HREC.

Figure 6:
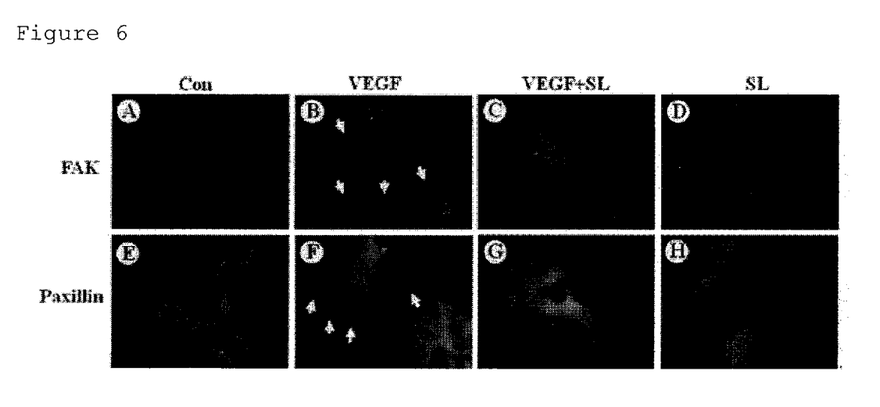
FIG. 6 shows fluorescence micrographs showing sialyllactose's inhibition effect of VEGF-induced assembly having focal adhesions in HREC [White arrows represent stained anti-FAK (B) and anti-paxillin (F) dot clusters, respectively.]

Sialyllactose's Inhibition Effect Against VEGF-induced Assembly Having Focal Adhesions in HREC Sialyllactose's effect on focal adhesions formed by VEGF-stimulated FAK and paxillin tyrosine phosphorylation was further investigated. HREC were stimulated with 50 ng/mL VEGF in the presence or absence of sialyllactose. Anti-FAK stained dot clusters were indicated as white arrows. In VEGF-induced HREC, focal adhesions immunostained with anti-FAk increased (FIG. 6, B). However, focal adhesion was markedly inhibited by sialyllactose (FIG. 6, C). In the control group cells, strongly distributed paxillin immunofluorescence staining was observed at the areas presumed to be around the nuclei. Strongly stained focal adhesion-like structures were seen, but the number was relatively small (FIG. 6, F). Sialyllactose certainly blocked the recruitment and increase of anti-paxillin immunostaining of focal adhesions in VEGF-stimulated HREC (FIG. 6, G).

Figure 7:
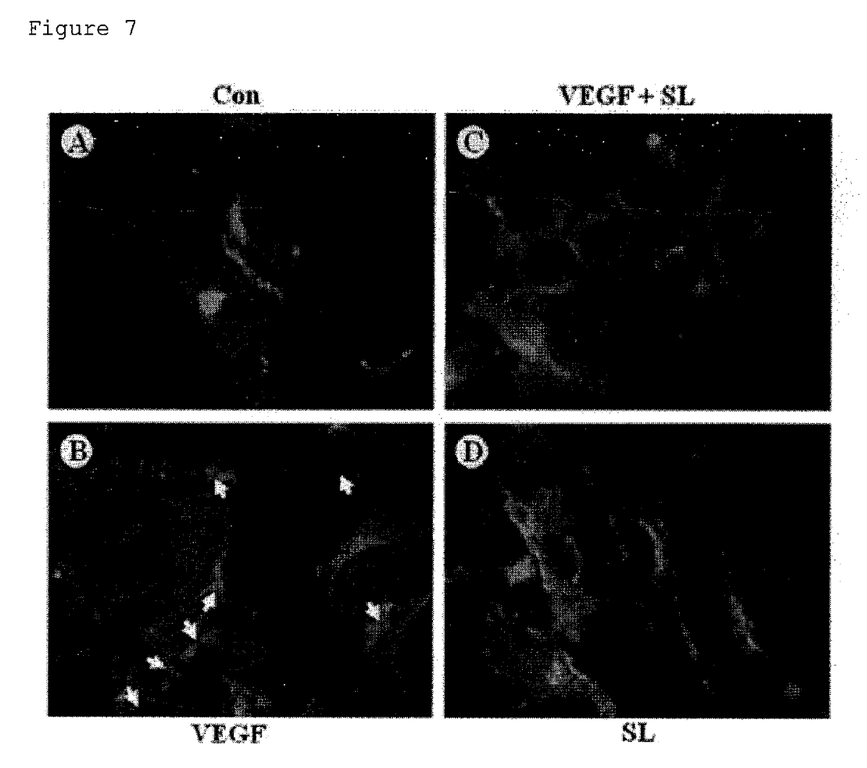
FIG. 7 shows fluorescence micrographs showing sialyllactose's inhibition effect of VEGF-induced intercellular adhesion in HREC [White arrows represent cleavage of sialyllactose by ceramide glycanase.].

Increased endothelial cell monolayers associated with the increased tyrosine phosphorylation reduces intercellular adhesion, and increases VEGF-induced mobility and permeability of epithelial cells in human umbilical vein endothelial cells (HUVEC) (28-30). Accordingly, the inventors of the present invention investigated whether sialyllactose could change the level of phosphorylation and, thereby, change such effect in HUVEC. In unstimulated long-confluent monolayers, the phosphotyrosine signal spread well over widely overlapped cell areas, and only the focal adhesions showed weak staining (FIG. 7, A). One hour after VEGF stimulation, the phosphotyrosine labeling pattern was strikingly changed. The VE-cadherin staining was redistributed in a zigzag pattern (FIG. 7, B). The sharp and continuous intercellular contact areas shown in VEGF-stimulated intercellular adhesion in HREC were recovered by sialyllactose (FIG. 7, C). These results show that sialyllactose effectively inhibits anti-paxillin immunostaining at focal adhesions and intercellular adhesions in HREC.

As described in detail above, the present invention provides a composition for prophylaxis or treatment of eye disease comprising the compound represented by General Formula I as an effective ingredient. The compound used as the effective ingredient of the present invention inhibits expression of MMP-9 and inflammation-mediated cytokines (IL-1β, TNF-α, etc.) in corneal epithelial cells and inhibits VEGF-mediated VEGFR-2 activation in HREC, thereby exhibiting prophylactic or therapeutic activity for eye diseases such as dry eye syndrome, inflammatory eye disease, neovascularization-associated eye disease and side effects of wearing of contact lenses. Also, because it has no cytotoxicity or skin side effect, the composition of the present invention may be safely used as a pharmaceutical composition, a neutraceutical composition or a food composition. In addition, the composition of the present invention may be used as a cleaner or a lubricant for contact lenses since it has nonbacterial antiinflammatory activity and ocular contact lubricating activity.

While the present invention has been described with respect to the specific embodiments, it will be apparent to those skilled in the art that various changes and modifications may be made without departing from the spirit and scope of the invention as defined in the following claims.

REFERENCES

1. K. B. Bjerrum, Keratoconjunctivitis sicca and primary Sjogren's syndrome in a Danish population aged 30-60 years. *Acta Ophthalmol, Scand.* 1997; 75:281286.

2. C. A. McCarty, A. K. Bansal, P. M. Livingston, Y. L. Stanislaysky and H. R. Taylor, The epidemiology of dry eye in Melbourne, Australia, *Ophthalmology* 1998; 105: 11141119.
3. E. Goto, Y. Yagi, Y. Matsumoto and K. Tsubota, Impaired functional visual acuity of dry eye patients, *Am. J. Ophthalmol.* 2002; 133:181186.
4. S. C. Pflugfelder, S. C. G. Tseng, O, Sanabria, H. Kell, C. G. Garcia, C. Felix, W. Feuer and B. L. Reis, Evaluation of subjective assessments and objective diagnostic tests for diagnosing tear-film disorders known to cause ocular irritation, *Cornea* 1998; 17:3856.
5. C. Baudouin, H. Liang, D. Bremond-Gignac, P. Hamard, R. Hreiche, C. Creuzot-Garcher, J. M. Warnet and F. Brignole-Baudouin, CCR 4 and CCR 5 expression in conjunctival specimens as differential markers of T(H)1/T(H)$_2$ in ocular surface disorders, *J. Allergy Clin. Immunol.* 2005; 116:614619.
6. M. Rolando, S. Barabino, C. Mingari, S. Moretti, S. Giuffrida and G. Calabria, Distribution of conjunctival HLA-DR expression and the pathogenesis of damage in early dry eyes, *Cornea* 2005; 24:951954.
7. R. Kaswan, M. Salisbury, A new perspective on canine keratoconjunctivitis sicca: treatment with ophthalmic cyclosporine, *Vet Clin North Am Small Anim Pract.* 1990; 20:583613.
8. Jehangir S. Dry eye syndrome in a Pakistani community, *J Pak Med. Assoc.* 1990; 40:6667.
9. L. Sobrin, Z. Liu, D. C. Monroy, A. Solomon, M. G. Selzer, B. L. Lokeshwar and S. C. Pflugfelder, Regulation of MMP-9 activity in human tear fluid and corneal epithelial culture supernatant, *Invest. Ophthalmol. Vis. Sci.* 2000; 41:17031709.
10. S. Pflugfelder, W. Farley, L. Luo, L. Chen, C. de Paiva, L. C. Olmos, D. Q. Li and M. E. Fini, Matrix metalloproteinase-9 knockout confers resistance to corneal epithelial barrier disruption in experimental dry eye, *Am. J. Pathol.* 2005; 166:6171.
11. Pflugfelder S C. Anti-inflammatory therapy of dry eye, *Am J Ophthalmol.* 2004; 137:337342.
12. D.-Q. Li, Z. Chen, X. J. Song, W. J. Farley and S. C. Pflugfelder, Hyperosmolarity stimulates production of MMP-9, IL-1β and TNF-by human corneal epithelial cells via a c-Jun NH2-terminal kinase pathway, Invest. *Ophthalmol. Vis. Sci.* 2002; 43:539-549.
13. S. C. Pflugfelder, S. C. Tseng, K. Yoshino, et al. Correlation of goblet cell density and mucosal epithelial membrane mucin expression with rose bengal staining in patients with ocular irritation. *Ophthalmology* 1997; 104: 223-35.
14. Hanahan D, Folkman J. Patterns and emerging mechanisms of the angiogenic switch during tumorigenesis. *Cell,* 1996; 86:353-364.
15. Risau W. Mechanisms of angiogenesis. *Nature (Lond.),* 1997; 386:671-674.
16. Penn J S, McCollum G W, Barnett J M, Werdich X Q, Koepke K A, Rajaratnam V S. Angiostatic effect of penetrating ocular injury: role of pigment epithelium-derived factor. *Invest Ophthalmol Vis Sci.,* 2006; 47:405-414.
17. Kalebic T, Garbisa S, Glaser B, Liotta L A. Basement membrane collagen: degradation by migrating endothelial cells. *Science.* 1983; 221:281283.
18. Bellon G, Martiny L, Robinet A. Matrix metalloproteinases and matrikines in angiogenesis. *Crit. Rev Oncol Hematol.* 2004; 49:203220.
19. Folkman J. Angiogenesis in cancer, vascular, rheumatoid and other disease. *Nat. Med.,* 1995, 1:27-31.
20. Doherty M J, Canfield A E. Gene expression during vascular pericyte differentiation. *Crit. Rev Eukaryot Gene Exp.* 1999; 9:117.
21. H. Lis and N. Sharon. Lectins: Carbohydrate-Specific Proteins That Mediate Cellular Recognition, *Chem. Rev.* 1998; 98:637-645.
22. O. T. Eppler, R. Horstkorte, M. Pawlita, C. Schmidt and W. Reutter. Biochemical engineering of the N-acyl side chain of sialic acid: biological implications, *Glycobiology* 2001; 11:11-18.
23. L. Luo, D. Q. Li, A. Doshi, W. Farley, R. M. Corrales, S. C. Pflugfelder. Experimental dry eye stimulates production of inflammatory cytokines and MMP-9 and activates MAPK signaling pathways on the ocular surface, *Invest Ophthalmol Vis Sci.* 2004; 45:4293-301.
24. L. Sobrin, Z. Liu, D. C. Monroy, A. Solomon, M. G. Selzer, B. L. Lokeshwar, S. C. Pflugfelder. Regulation of MMP-9 activity in human tear fluid and corneal epithelial culture supernatant. *Invest Ophthalmol Vis Sci.* 2000; 41:17031709.
25. Matsumoto T, Claesson-Welsh L. VEGF receptor signal transduction. *Sci STKE.* 2001; 11.
26 Gille H, Kowalski J, Li B, LeCouter J, Moffat B, Zioncheck T F, Pelletier N, Ferrara N. Analysis of biological effects and signaling properties of Flt-1 (VEGFR-1) and KDR (VEGFR-2). A reassessment using novel receptor-specific vascular endothelial growth factor mutants. *J Biol. Chem.* 2001; 276:3222-30.
27. Gerber H P, McMurtrey A, Kowalski J, Yan M, Keyt B A, Dixit V, Ferrara N. Vascular endothelial growth factor regulates endothelial cell survival through the phosphatidylinositol 3'-kinase/Akt signal transduction pathway. Requirement for Flk-1/KDR activation. *J Biol. Chem.* 1998; 273:30336-30343.
28. Abedi H, Zachary I. Vascular endothelial growth factor stimulates tyrosine phosphorylation and recruitment to new focal adhesions of focal adhesion kinase and paxillin in endothelial cells. *J Biol. Chem.* 1997; 272:15442-15451.
29. Shibamoto, S., Hayakawa, M., Takeuchi, K., Hori, T., Oku, N., Miyazawa, K., Kitamura, N., Takeichi, M. and Ito, F. Tyrosine phosphorylation of beta-catenin and plakoglobin enhanced by hepatocyte growth factor and epidermal growth factor in human carcinoma cells. *Cell Adhes. Commun.* 1994; 1:295-305.
30. Esser S, Lampugnani M G, Corada M, Dejana E, Risau W. Vascular endothelial growth factor induces VE-cadherin tyrosine phosphorylation in endothelial cells. *J Cell Sci.* 1998; 111:1853-65.
31. L. D. Barber, S. C. Pflugfelder, J. Tauber, G. N. Foulks. Phase III safety evaluation of cyclosporine 0.1% ophthalmic emulsion administered twice daily to dry eye disease patients for up to 3 years. *Ophthalmology* 2005; 112: 1790-4.
32. C. S. de Paiva, J. L. Lindsey and S. C. Pflugfelder, Assessing the severity of keratitis sicca with videokeratoscopic indices, *Ophthalmology* 2003; 110:11021109.
33. A. M. Terres, J. M. Pajares, A. M. Hopkins, A. Murphy, A. Moran, A. W. Baird and D. Kelleher, *Helicobacter pylori* disrupts epithelial barrier function in a process inhibited by protein kinase C activators, *Infect. Immun.* 1998; 66: 29432950.

The invention claimed is:
1. A method for treatment of an eye disease comprising administering a composition comprising a compound represented by Formula I or a salt thereof to a subject in need of such treatment, wherein the eye disease is dry eye syndrome, inflammatory eye disease, retinal neovascularization-associated eye disease, or side effects of wearing of contact lenses:

$$S\text{-}(MS)_p\text{-}(MS)_q \qquad \text{Formula I}$$

wherein S represents sialic acid, and $(MS)_p$ and $(MS)_q$ independently represent a monosaccharide residue.

2. The method according to claim 1, wherein $(MS)_p$ represents galactose and $(MS)_q$ represents glucose.

3. The method according to claim 1, wherein the inflammatory eye disease is selected from a group consisting of meibomian gland dysfunction, Stevens-Johnson syndrome, Sjogren's syndrome, uveitis, and keratitis.

4. The method according to claim 1, wherein the retinal neovascularization-associated eye disease is selected from the group consisting of diabetic retinopathy, macular degeneration, retinopathy of prematurity, corneal graft rejection, and neovascular glaucoma.

5. The method according to claim 4, wherein the composition inhibits retinal neovascularization by inhibiting VEGF-mediated VEGFR-2 activation in human retinal endothelial cells.

6. The method according to claim 1, wherein the composition is a pharmaceutical composition.

7. The method according to claim 6, wherein the composition is in the form of a solution, suspension, syrup, emulsion, liposome, dust, powder, granule, tablet, sustained-release formulation, eye drop, capsule, contact lens cleaner or contact lens lubricant.

8. A method for lubricating or hydrating an eye in a subject in need thereof comprising topically applying an artificial tear composition comprising a compound represented by Formula I or a salt thereof to an eye of the subject:

$$S\text{-}(MS)_p\text{-}(MS)_q \qquad \text{Formula I}$$

wherein S represents sialic acid, and $(MS)_p$ and $(MS)_q$ independently represent a monosaccharide residue.

9. The method according to claim 8, wherein $(MS)_p$ represents galactose and $(MS)_q$ represents glucose.

10. The method according to claim 8, wherein the active ingredient promotes secretion of tears from the lachrymal gland.

11. A method for cleaning, lubricating, or packaging contact lenses comprising contacting a composition comprising a compound represented by Formula I or a salt thereof with contact lenses:

$$S\text{-}(MS)_p\text{-}(MS)_q \qquad \text{Formula I}$$

wherein S represents sialic acid, and $(MS)_p$ and $(MS)_q$ independently represent a monosaccharide residue.

* * * * *